United States Patent
Muller

(10) Patent No.: US 6,176,859 B1
(45) Date of Patent: *Jan. 23, 2001

(54) PULLING APPARATUS FOR CORRECTING A JAW

(76) Inventor: Paul A. Muller, Bellerive Str. 34 CH-8034, Zurich (CH)

( * ) Notice: Under 35 U.S.C. 154(b), the term of this patent shall be extended for 0 days.

This patent is subject to a terminal disclaimer.

(21) Appl. No.: 09/256,483

(22) Filed: Feb. 23, 1999

(51) Int. Cl.$^7$ ................................................. A61B 17/56
(52) U.S. Cl. ................................................ 606/53; 433/140
(58) Field of Search ...................... 606/53, 69, 70–73, 606/54, 57–58, 60, 103, 105; 433/140, 172, 173, 176

(56) References Cited

U.S. PATENT DOCUMENTS

| | | | |
|---|---|---|---|
| 2,587,245 | * | 2/1952 | Terre ........................................ 606/57 |
| 3,927,664 | * | 12/1975 | Georgiade et al. ..................... 128/76 |
| 4,232,660 | * | 11/1980 | Coles ...................................... 128/20 |
| 5,540,687 | * | 7/1996 | Fairley et al. .......................... 606/60 |
| 5,885,283 | * | 3/1999 | Gittleman ............................... 606/57 |
| 5,885,289 | * | 3/1999 | Muller .................................... 606/71 |

FOREIGN PATENT DOCUMENTS

19538323 * 4/1997 (DE) ................................ A61C/7/10

* cited by examiner

Primary Examiner—Michael Buiz
Assistant Examiner—Jonathan D. Goldberg
(74) Attorney, Agent, or Firm—Bachman & LaPointe, P.C.

(57) ABSTRACT

In a pulling apparatus for correcting a jaw on a skull, for instance for the elimination of a supraclusion, cross bite or cleft palate, a basic member is provided with elements for attachment to the jaw and is movable in the correcting direction ($x_1$). The basic member is to be movable also in a direction deviating from the correcting direction ($x_1$).

8 Claims, 1 Drawing Sheet

PULLING APPARATUS FOR CORRECTING A JAW

BACKGROUND OF THE INVENTION

The present invention relates to a pulling apparatus for correcting a jaw on a skull for instance in order to eliminate a supraclusion, cross bite or cleft palate, a basic member being provided with elements for attachment to the jaw and being movable in the direction of correction.

Such a pulling apparatus is known from German Patent Publication 195 38 323, which corresponds to U.S. Pat. No. 5,885,289. It is the object of the present invention to improve said pulling apparatus and make it more variable.

SUMMARY OF THE INVENTION

This object can be achieved due to the fact that the basic member can also be moved in a direction deviating from the correcting direction.

It has been found that the setting of the correcting direction is of great importance. The correcting direction should, in this connection, not only be established at the beginning of the treatment, but it should also be variable over the course of the treatment and it should be possible to adapt it to changing conditions. This is only possible if the basic member can also be moved in a direction deviating from the correcting direction, as is the case in accordance with the present invention. This means that the basic member and thus the direction of pull can be adapted to changing conditions. This is the basic concept of the present invention and constitutes a substantial advantage.

How this mobility of the basic member in a direction differing from the correcting direction can be achieved is of secondary importance as compared with this basic inventive concept, but a preferred embodiment will be described below:

BRIEF DESCRIPTION OF THE DRAWING

The present invention will be more readily understood from a consideration of the accompanying drawing.

DETAILED DESCRIPTION OF PREFERRED EMBODIMENTS

Figure 1:
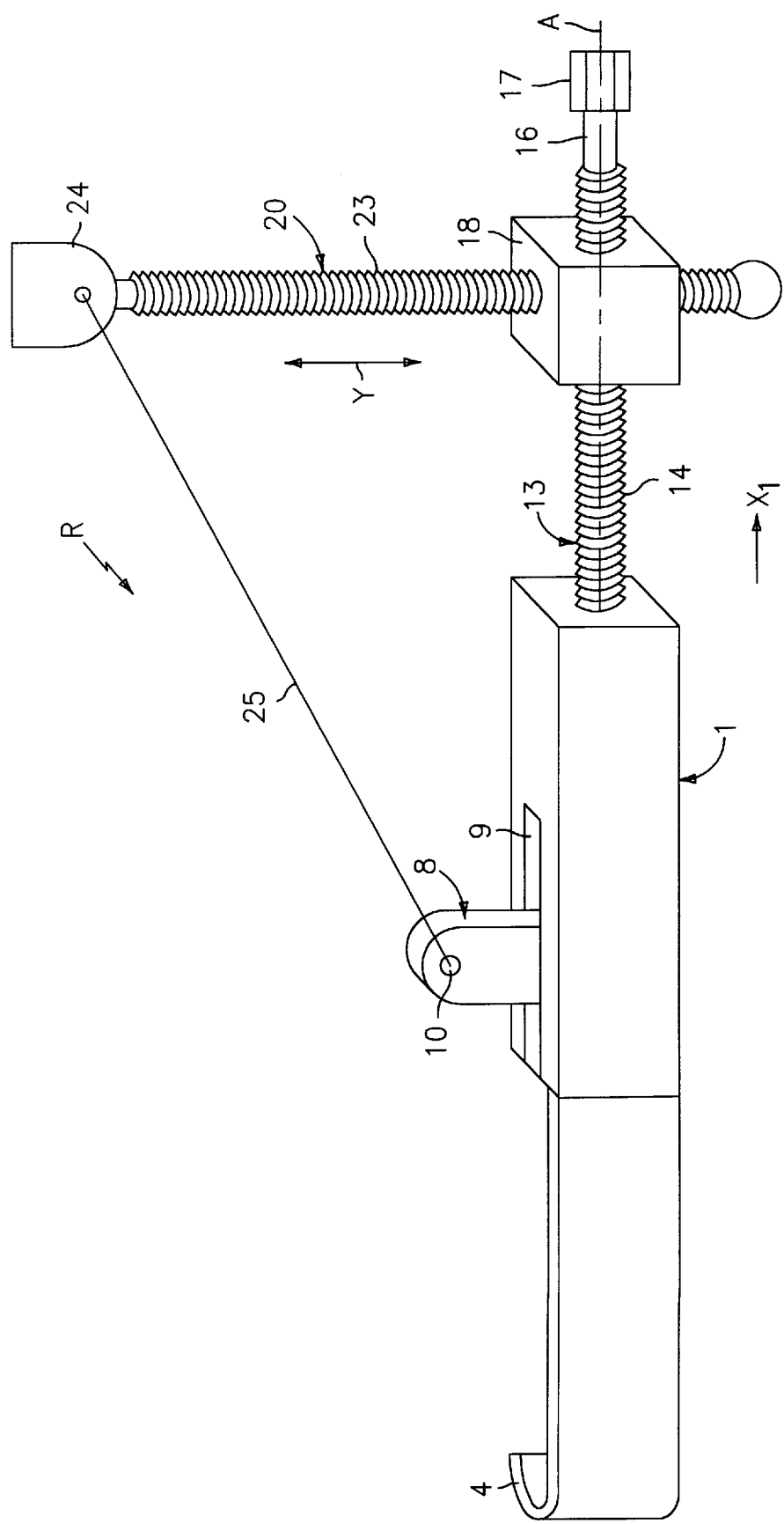
FIG. 1 is a side view.

It is already known from German Patent Publication 195 38 323 that the basic member has a connecting element with respect to which the basic member can be moved in the correcting direction and which has a fixed connection to a permanent fixation on the jaw and/or skull itself. This permanent fixation effects an approximate basic attachment of the entire pulling apparatus on the skull. The connecting element itself maintains as a rule a constant distance from the permanent fixation, while the basic member can be displaced relative to the connecting element. This takes place by means of a drive which is described in German Patent Publication 195 38 323. Reference is therefore had to this document, and it is also made an integral part of the present application.

A mobile fixation is preferably placed on German Patent Publication said actuating element, an external thread of the actuating element extending also through said mobile fixation so that, upon a turning of the actuating element, the mobile fixation travels along the thread and any distance between mobile fixation and basic member is not changed.

Approximately perpendicular to the actuating element, the mobile fixation is passed through by a connection whose one end is attached to the permanent fixation. The connection is developed in such a manner that the mobile fixation can be moved along it. For the sake of simplicity, a thread section is provided also in this case which section passes through a corresponding hole with internal thread in the mobile fixation. Upon a turning of this thread section, the mobile fixation can now travel along said section.

As mentioned above, many varieties of such a connection are conceivable and are to be covered by the present invention.

It is an essential advantage of the present invention that, by means of the connection between the permanent fixation and the mobile fixation, a direction of pull can be set which is then no longer changed upon a turning of the actuating element. It can only be changed again upon an actuating of the connection itself. This can be done at any time in the course of the treatment.

Thus, upon a pull which acts on the maxilla in the direction towards the front, the swinging open movement of the maxilla in downward or upward direction can be controlled or else prevented, and this merely by actuating the connection between the permanent fixation and the mobile fixation.

Further advantages, features and details of the invention result from the following description of preferred embodiments and from the drawing; the latter shows in its sole figure a perspective view of a pulling apparatus according to the invention on a permanent fixation.

A pulling apparatus R according to the invention, whose function will be described further below, has, in accordance with the accompaning drawing, a basic member 1. A hook 4 adjoins said basic member 1. As described further below, said hook 4 engages on one side behind a maxilla.

The basic member 1 has, as described in German Patent Publication 195 38 323, a through-hole which receives a slide which is movable primarily in a direction opposite the correcting direction $x_1$.

At one end a connecting element 8 is placed on the slide, said connecting element extending out of the basic member 1 from a slot 9. The connecting element 8 has a hole 10 which serves to receive a holding element described further below.

At the other end of the connecting element 8 the slide has a frontal blind hole into which a pin is inserted. The pin rotates freely in the blind hole and is part of an actuating element 13 by means of which the slide is moved. For this purpose, the actuating element 13 has a thread section 14 with external thread which meshes with an internal thread in the through-hole, not shown in detail.

A rod section 16 adjoins the thread section 14, the rod section terminating in a hexagon 17. When this hexagon 17 is acted on by a corresponding tool, the actuating element 13 can be turned around its longitudinal axis A, it rotating freely with respect to the slide. Via the external thread, the actuating element 13 is, however, screwed further into the through-hole so that it moves the slide in a direction opposite the correcting direction $x_1$ which results in a movement of the basic member 1 in the correcting direction $X_1$.

On the actuating element 13 there is a mobile fixation 18 which is movable along the actuating element 13. This mobile fixation 18 is passed through by a connection 20 which establishes a connection with a permanent fixation 24. This permanent fixation 24 can, for instance, be a titanium platelet which, as mentioned in German Patent Publication 195 38 323, is attached to another part of the maxilla or of the skull. It is essential that as a result of this connection 20 the mobile fixation 18 can be moved in the direction y with respect to fixation 24.

In the embodiment shown, the connection 20 has an external thread 23. The mobile fixation 18 travels on said external thread 23.

The manner of operation of the present invention is as follows:

As described in German Patent Publication 195 38 323.0 the pulling apparatus R is, for instance, so applied to a maxilla of a human skull that the hook 4 engages behind the last molar of the maxilla. The connecting element 8 is connected, for instance by a wire 25, to the permanent fixation 24 on the jaw or skull. An adjustment of the direction of pull now takes place, i.e. as a rule an adjustment of the correcting direction by the connection 20 since the position of the basic member 1 can be defined exactly by said connection 20.

In order to exert a pull on the maxilla, the actuating element 13 is turned as described in German Patent Publication 195 38 323. The connecting element 8 is thereby displaced in a direction opposite the correcting direction $x_1$ and the basic member 1 and thus also the hook 4 are thus displaced in correcting direction. At the same time, however, the mobile fixation also moves in a direction opposite the correcting direction $x_1$ so that the pulling direction, once adjusted, is not changed even upon a further turning of the actuating element 13.

What is claimed is:

1. A pulling apparatus for correcting a jaw on a skull in order to eliminate a supraclusion, cross bite or cleft palate, which comprises: a basic member movable in the direction of correction ($x_1$); elements connected to said basic member for attachment to the jaw; wherein the basic member is also movable in a direction deviating from the correcting direction ($x_1$); and wherein the basic member has a connecting element connected thereto with respect to which the basic member is movable in the correcting direction ($x_1$), and which connecting element has a fixed connection to a permanent fixation member, wherein said apparatus exerts pulling on the jaw for correcting the jaw.

2. A pulling apparatus according to claim 1, wherein a connection member is connected to the permanent fixation member, and wherein the basic member is movable in a direction along the connection member.

3. A pulling apparatus according to claim 2, including a further element connected to the basic member, wherein the basic member is movable along the further element.

4. A pulling apparatus according to claim 3, wherein said further element is an actuating element, and including a mobile fixation member placed on said actuating element and being passed through by said connection member, with the permanent fixation member affixed to said connection member.

5. A pulling apparatus according to claim 4, wherein the actuating element includes a thread section along which the mobile fixation member can be moved.

6. A pulling apparatus according to claim 4, wherein the connection member includes an external thread on which the mobile fixation member moves.

7. A pulling apparatus according to claim 1, wherein said direction deviating from the correcting direction ($x_1$) is a direction opposed to the correcting direction.

8. A pulling apparatus according to claim 1, wherein the fixed connection is a wire.

* * * * *